United States Patent [19]

Bridger

[11] Patent Number: 5,702,951
[45] Date of Patent: Dec. 30, 1997

[54] CONTINUOUS RBCOD MEASUREMENT

[75] Inventor: John Stephen Bridger, Forest Hill, Australia

[73] Assignee: Commonwealth Scientific and Industrial Research Organisation, Campbell, Australia

[21] Appl. No.: 310,793

[22] Filed: Sep. 29, 1994

Related U.S. Application Data

[63] Continuation of Ser. No. 962,785, filed as PCT/AU91/00287, Jul. 31, 1991, abandoned.

[30]     Foreign Application Priority Data

Jul. 4, 1990 [AU] Australia .................................. PK0974

[51] Int. Cl.$^6$ ............................................ G01N 33/18
[52] U.S. Cl. ........................ 436/62; 436/138; 422/79; 435/286.1; 435/287.1; 210/614; 210/620
[58] Field of Search .................... 436/62, 138; 435/289, 435/291, 286.1, 287.1; 210/612, 614, 620, 219, 220, 221.1, 96.1; 422/79

[56]            References Cited

U.S. PATENT DOCUMENTS

| | | | |
|---|---|---|---|
| 3,731,522 | 5/1973 | Mikesell | 436/62 X |
| 4,162,195 | 7/1979 | Solyom et al. | 435/32 X |
| 4,329,232 | 5/1982 | McKenna | 436/62 X |
| 4,564,453 | 1/1986 | Coplot et al. | 210/614 |
| 4,622,134 | 11/1986 | Kobayashi | 210/220 X |
| 4,748,127 | 5/1988 | Siepmann et al. | 436/138 X |
| 5,017,496 | 5/1991 | Klapwijk et al. | 436/62 |
| 5,085,759 | 2/1992 | Harker | 204/408 |

FOREIGN PATENT DOCUMENTS

| | | |
|---|---|---|
| 2952343 | 6/1981 | Germany . |
| 56-108951 | 8/1981 | Japan . |
| 57-135357 | 8/1982 | Japan . |
| 59-99353 | 6/1984 | Japan . |
| 61-129567 | 6/1986 | Japan . |
| 1133553 | 1/1985 | U.S.S.R. . |
| 2184110 | 12/1986 | United Kingdom . |

OTHER PUBLICATIONS

Lindrea et al, Australian Water and Wastewater Assoc. 13th Federal Convention, pp. 294–298 (Mar. 6–10, 1989).

Sollfrank et al, GWF DAS GAS–UND Wasserfach, vol. 126, No. 8, pp. 397–405 (Aug. 1985) (English translation).

"Biological Treatment of Waste–Water" M. A. Winkler, et al; Advanced Activated Sludge Processes (Ch. 5), 1981.

*Primary Examiner*—Maureen M. Wallenhorst
*Attorney, Agent, or Firm*—Birch, Stewart, Kolasch & Birch, LLP

[57]             ABSTRACT

The invention provides a method and apparatus for providing periodical measurements of the real-time readily biodegradable chemical oxygen demand (RBCOD) of a wastewater stream. The apparatus includes a bio-reactor having an inlet for accepting a feed from the stream and an overflow outlet, whereby a sample volume can be maintained within the reactor. A feed rate is chosen to ensure an hydraulic retention time (HRT) in the reactor sufficient for substantially complete oxidation of the readily biodegradable compounds in the feed. Air is periodically passed through the sample volume for set periods and the oxygen up-take (OUR) is determined by measuring the dissolved oxygen content via a probe during the air-off periods. An RBCOD value is then calculated for each OUR value. The invention may be used to monitor the performance of wastewater treatment plants.

11 Claims, 8 Drawing Sheets

OXYGEN UPTAKE in CONTINUOUS REACTOR due to ACETATE ADDITION

OXYGEN UPTAKE of APT INFLUENT and EFFLUENT

[November 89 Sludge Age = 1 Day]

CONTINUOUS RBCOD MEASUREMENT

This application is a continuation of application Ser. No. 07/962,785 filed as PCT/AU91/00287 on Jul. 31, 1991, now abandoned.

TECHNICAL FIELD

This invention relates to the measurement of readily biodegradable chemical oxygen demand (RBCOD) in an effluent or wastewater. In particular, the invention relates to a method and apparatus for real-time monitoring of RBCOD in a wastewater stream or feed.

The RBCOD of a waste stream is important as it may affect the operation of a process for treating the waste. For example, in biological sewage treatment systems capable of excess phosphorus removal, it has been shown that an appropriate portion of the incoming chemical oxygen demand (COD) needs to be readily biodegradable (Fuhs, G. W. and Chen, M. (1975). "Phosphorus Removal Activated Sludge Process", Microbial. Ecology, 2, 119–139; Venter, S. L. V., Halliday, J. and Pitman, A. K. (1978). "Optimization of the Johannesburg Olifantzvlei Extended Aeration Plant for Phosphorus Removal", Prog Wat Tach, 10, 279–292). Where the RBCOD portion of the influent is found to be so low as not to achieve biological phosphorus removal, enrichment of the influent with fermentation products, such as volatile fatty acids (VFA) will be necessary. These products may come from solids settled from the sewage or from an external source such as digester sludge, industrial or agricultural waste.

The need for a continuous on-line method of monitoring the RBCOD in the feed to a sewage treatment plant for process control has been recognised. For example H. A. Nichols, C S Stevens and S Deacon in their paper "Full Scale Experimentation: Comparison of Different Control Strategies" published in the Papers of Technology Transfer Symposium "Advances in Biological Phosphorous Removal by the Activated Sludge Process" 27 Oct. 1988 Water Research Commission of South Africa, state the following:

"There is an urgent need . . . to develop a good and reliable method of monitoring the readily biodegradable COD in the [sewage] feed, so that not only the performance of primary sedimentation tanks can be monitored, but also the performance of the activated sludge process itself."

RBCOD measurements are also useful to monitor the performance of treatment processes, whether or not they have been designed for excess phosphorus removal. Thus there is a need for measurement of the RBCOD of wastewater both up-stream and down-stream of a treatment plant. Furthermore the RBCOD of an effluent stream may assist in characterising that stream for design of a suitable treatment plant therefor.

Knowledge of RBCOD levels is also useful for the control of anaerobic digesters where an increase in RBCOD may indicate microbial imbalance within the digester.

BACKGROUND ART

Both biological and physical methods are known for measurement of RBCOD. Physical methods involving COD measurement of membrane filtered samples have given poor correlation with biological methods. The three main biological methods are 1) the short sludge age, step fed reactor, 2) the batch aerobic reactor and 3) the batch anaerobic reactor. These are described in some detail by Dold at. al. "Comparison of Measurement Methods for Readily Biodegradable COD Fraction in Municipal Wastewater", IWPC, Durban, South Africa (1985).

The short sludge-age step fed reactor method has been reported as not giving consistent results and as being tedious, difficult to operate and unsuitable for the determination of in situ generated RBCOD. Furthermore, to obtain an RBCOD value representative of a 24 hour period, a large refrigerated composite sample would have to be collected each day. Long periods, for example 24 hours, are required for each measurement. Although measurement times can be reduced to about two hours with a batch aerobic reactor, the sampling and sample storage requirements for use of these reactors limit their applicability. The usefulness of anaerobic batch reactors is also limited by their sampling requirements. Furthermore RBCOD measurements based on limited sampling may not provide an accurate profile of the RBCOD of a waste stream because of wide variations over the diurnal cycle. Thus existing biological tests to determine RBCOD are not suitable for on-line or real-time monitoring of the influent to a treatment process or the effluent therefrom because they require a long time (2–24 hours) to obtain a result and the taking and storage of samples.

DISCLOSURE OF THE INVENTION

An object of this invention is to provide a method and apparatus allowing relatively quick measurements of the RBCOD of a wastewater stream or feed to be periodically taken.

By virtue of the invention it is possible to obtain almost "real-time" measurements of the RBCOD of a wastewater feed or stream such that the invention may be applied for monitoring, control or other purposes. For example, apparatus according to the invention could be left unattended for a period for relatively frequent data collection.

According to the invention there is provided a method for periodically determining the readily biodegradable chemical oxygen demand (RBCOD) in a wastewater stream or feed comprising:

i) continuously feeding a sample representative of the real-time wastewater stream or feed to a sample volume whereby the feed rate is controlled to ensure an hydraulic retention time (HRT) in the sample volume sufficient for substantially complete oxidation of the readily biodegradable compounds, ii) periodically passing air for predetermined periods through the sample volume, iii) determining the oxygen consumption in the sample volume by measuring a change in the dissolved oxygen content while not passing air through the sample volume, and iv) calculating an RBCOD value from each oxygen consumption measurement.

In accordance with the invention, it is not a requirement that sludge be added to that sample as in prior art RBCOD measurements. Thus the method can be used for monitoring sewers at any point in a sewage network.

The invention also provides apparatus for monitoring a wastewater stream or feed comprising:

i) a bio-reactor suitable for maintaining a completely mixed sample volume and for continually receiving a sample representative of the real-time wastewater feed, ii) air injection means which may be periodically operated to pass air for a predetermined period through a waste water sample when contained in the bio-reactor, iii) means for measuring the dissolved oxygen content of a sample within the bio-reactor to determine the oxygen consumption of the sample from which the readily biodegradable chemical oxygen demand (RBCOD) is calculable.

The bio-reactor (that is, the sample volume of the method aspect of the invention) is completely mixed and as the hydraulic retention time (HRT) is chosen to ensure the RBCOD is substantially oxidized in the reactor, then the concentration of RBCOD within the reactor at any point in time will be close to zero. (There will be some oxygen demand by the bacteria just for them to survive—this is called endogenous oxygen uptake, which in the practice of the invention, may be assumed to be constant.) It follows then that the oxygen consumption at any point in time is due to the incoming feed (plus the assumed constant endogenous demand).

An RBCOD value for each oxygen consumption measurement is calculated by multiplying the oxygen consumption measurement by a constant. Thus, soon after the start of an air-off period a first dissolved oxygen concentration measurement ($DO_1$) is taken and after a fixed period of time tp a second dissolved oxygen concentration measurement ($DO_2$) is taken from which the oxygen uptake consumption in the reactor in time $t_p$ is given by:

$$(DO_1 - DO_2) \times V = \Delta DO \times V mg$$

where V (liters) is the sample volume.

The RBCOD may be calculated from the change in dissolved oxygen concentration over the set measuring period by multiplying the value obtained by an apparatus constant which may be determined by calculation from the parameters of the system which are held fixed or by calibration using acetate solutions of known concentration as is shown below.

Thus RBCOD=$\Delta DO \times$constant.

The value for the constant includes a conversion factor of 3 for converting oxygen consumption to RBCOD (as suggested by Dold et al, supra) and factors relating the oxygen consumption in the bio-reactor over time $t_p$ to oxygen consumption in the quantity of the feed that enters the reactor. These factors include the feed rate into the bio-reactor, a constant measurement period $t_p$ and the bio-reactor volume.

BRIEF DESCRIPTION OF DRAWINGS

The invention will now be described, by way of example only, with reference to the accompanying drawings in which.

BEST MODE FOR CARRYING OUT THE INVENTION

Figure 1:
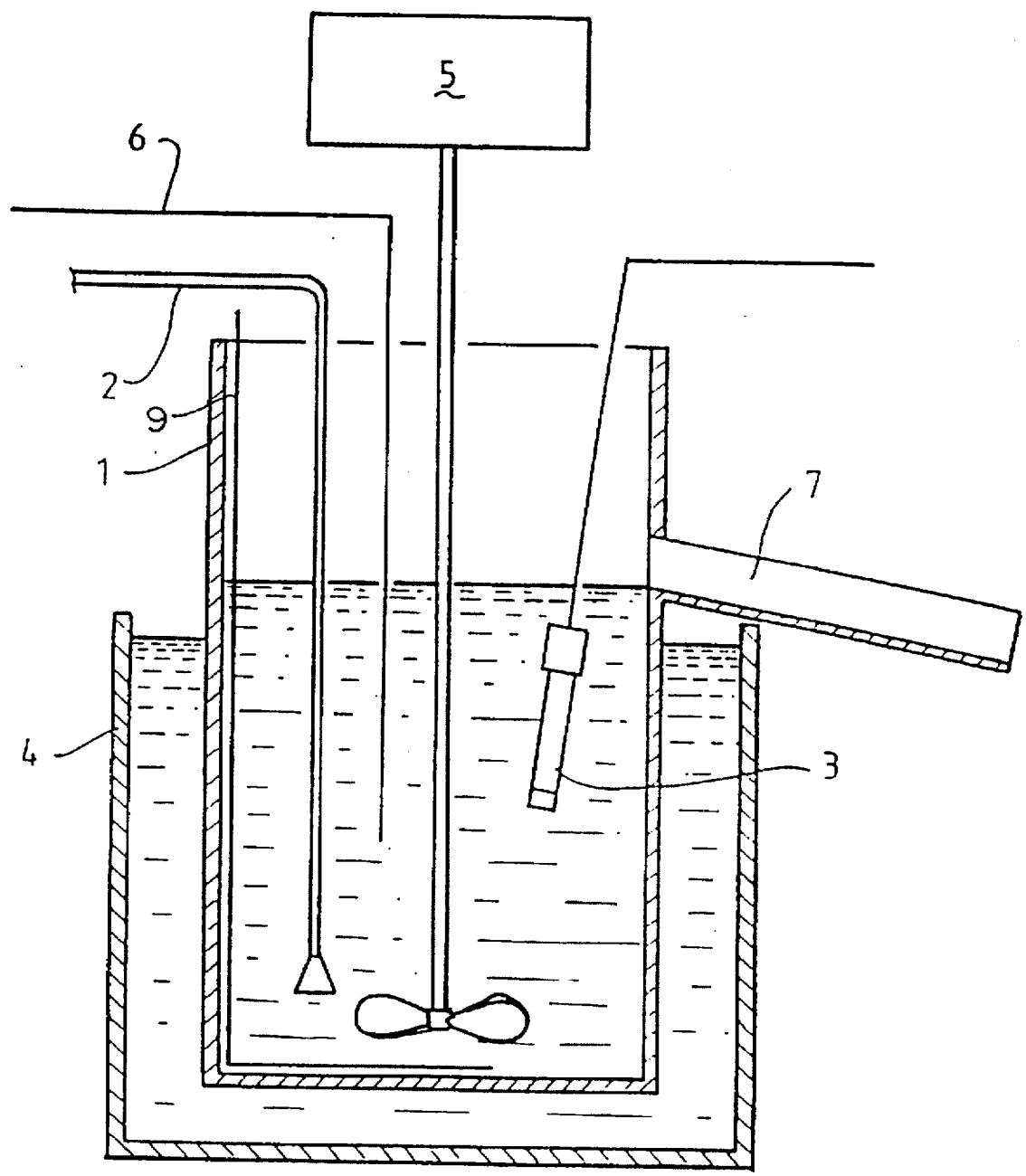
FIG. 1 is a diagrammatic sketch of apparatus according to the invention.

FIG. 1 illustrates example apparatus according to the invention. The apparatus comprises a 1.4 liter bioreactor 1 with an air injection means 2 and dissolved oxygen measuring probe 3. Associated with the bioreactor are temperature control means, in this case a water bath 4 maintained a 20° C., and a stirring means, for example a magnetic stirrer 5. An influent feed line is shown at 6 and overflow at 7. A temperature control means may not be required, for example in applications of the invention where the ambient temperature does not vary widely. Also, the bio-reactor may conveniently include means 9 to clean its internal surface, such as for example, a scraping means which is operable at selected intervals of time.

Figure 8:
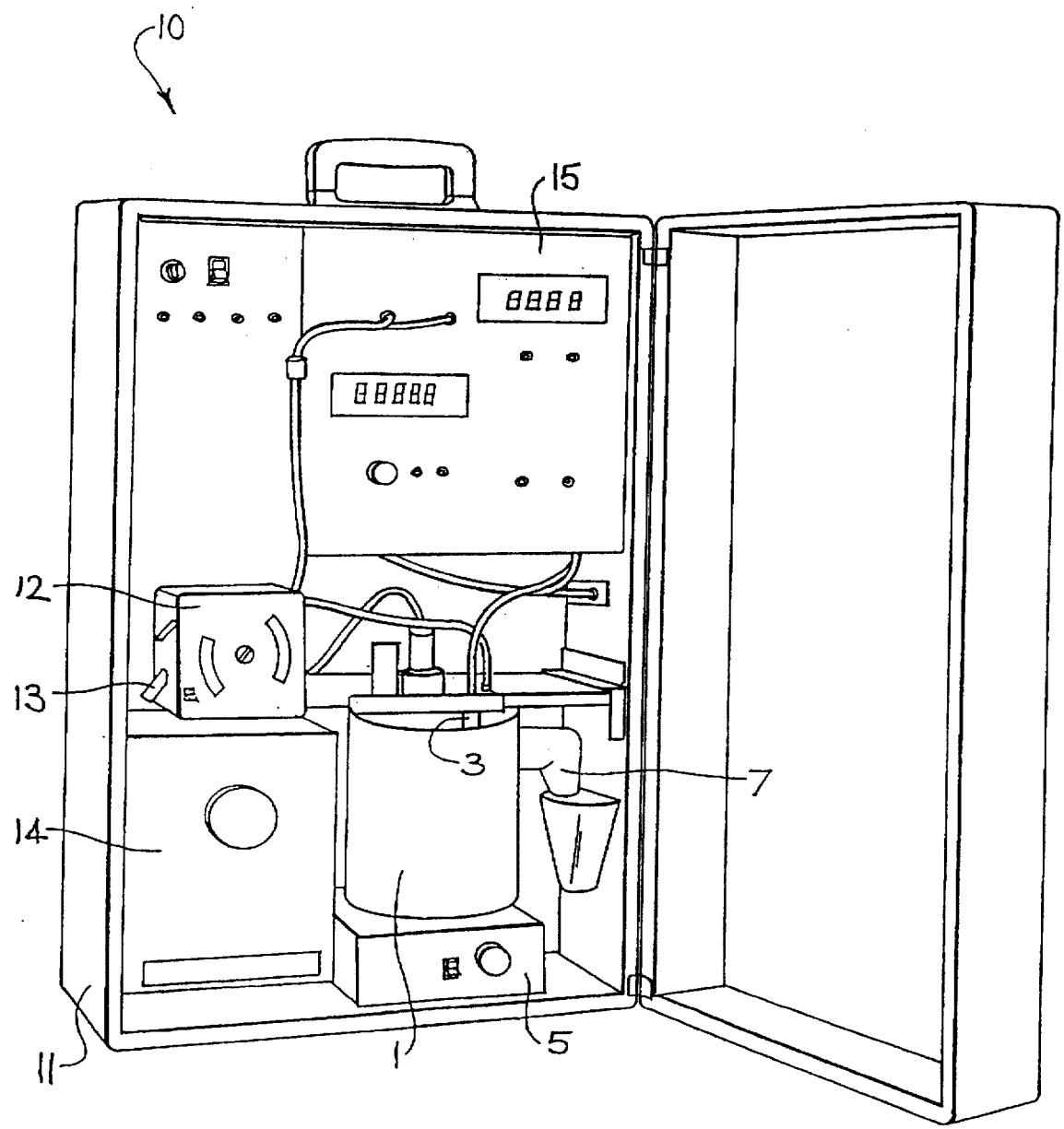
FIG. 8 illustrates apparatus according to the invention in the form of a self-contained portable unit.

The apparatus according to the invention may be supplied as a self contained portable unit, which unit may also include a data processing means for providing electrical output signals representative of RBCOD determinations. Optionally, such a portable unit may also include a pump connected to the bio-reactor input for supplying a constant feed thereto. Such a unit 10 is illustrated in FIG. 8 and comprises a housing 11 that contains a bio-reactor 1, a pumping arrangement 12 having an inlet 13 connectable to receive a waste water feed and for supplying a constant feed to the bio-reactor 1, an air pump 14 for supplying air to an air injector of the bio-reactor, a magnetic stirrer 5 for the bio-reactor, and a data processing device 15 for providing electrical output signals representative of RBCOD determinations. An overflow outlet for the bio-reactor is shown by reference 7 and reference manual 3 identifies the dissolved oxygen measuring probe in the bio-reactor.

Experimental Set Up

Two bio-reactors, each of 1.4 liters volume, were set up housed in a water bath at 20° C. and continuously fed by a peristaltic pump- The reactors were stirred at about 60 rpm. Since no attempt was made to retain solids, they acted as completely mixed reactors with the sludge age equal to the hydraulic retention time (HRT) which was around six hours. Air was applied in a 15 minute on, 15 minute off cycle at a rate chosen to prevent oxygen saturation occurring. (Any suitable on and off period for the air supply may be chosen, for example an on and off cycle of between 1 and 30 minutes may be chosen.) Measurement of dissolved oxygen (DO) was made by polarographic electrode connected to a flat bed chart recorder. This method and apparatus by which relatively quick periodical measurements of RBCOD may be taken is referred to herein as a "continuous" method or "continuous" reactor.

Care must be taken that the DO electrode's response rate is very much greater and its oxygen consumption rate very much smaller than the maximum and minimum oxygen uptake rates to be measured. The electrodes used were Titron 500MB with a response rate of around 2000 mg/l/hr and a consumption rate of <0.1 mg/l/hr. Maximum and minimum oxygen uptake rates in the reactors were in the order of 20 to 2 mg/l/hr.

So as to maintain a low endogenous oxygen uptake rate (OUR) in the reactor, cleaning of bio-film from all surfaces within the reactor was carried out once a day. The DO electrodes were likewise cleaned and calibrated to maintain their accuracy. Alternatively or additionally, the bio-reactor may include a cleaning means as has been described above.

Calibration of the reactors. To calibrate the oxygen uptake response of the continuous reactors, a comparison was made with an established batch method (ref. Lindrea et al - see below) by the addition of sodium acetate, expressed as acetic acid, to both the continuous reactors and a batch reactor. Plots of oxygen consumption rates following additions of acetate are shown for the batch method in FIGS. 2 and 3, and for the continuous method in FIGS. 4 and 5.

Sequential additions of acetate to both batch and continuous reactors result in similar shaped peaks in so much as the consumption rate increases with time. This may indicate that the population of bacteria is increasing to meet the available substrate or the bacterial population is being "switched on" due to the stimuli of the substrate. The area under the curve, or oxygen consumption, is similar for sequential additions to both types of reactor. A surprising feature was the low rate of degradation of the acetate substrate in the batch reactor, considering that it had a high biomass content compared to the continuous reactor.

The measured oxygen consumption for each peak is shown in Table 1 as a percentage of the theoretical chemical oxygen demand of the acetate added. No allowance has been made in the calculation for the acetate lost due to wash out from the continuous reactor, estimated to be between 10 and 15% of the acetate added.

TABLE 1

Figure 2:
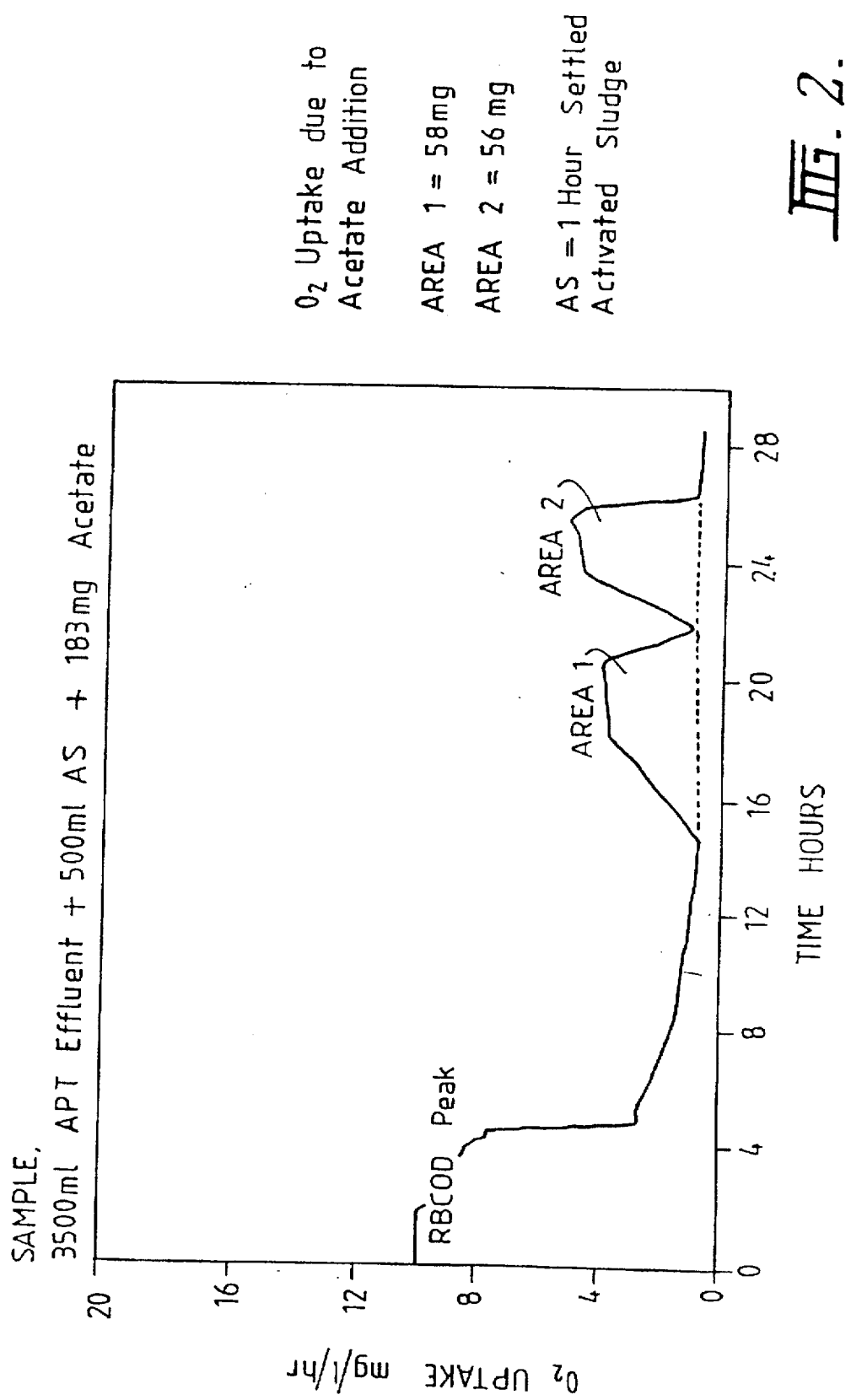
FIGS. 2 and 3 illustrate $O_2$ consumption of a batch reactor due to Acetate addition for comparison with and calibration of a reactor according to the invention.
Figure 3:
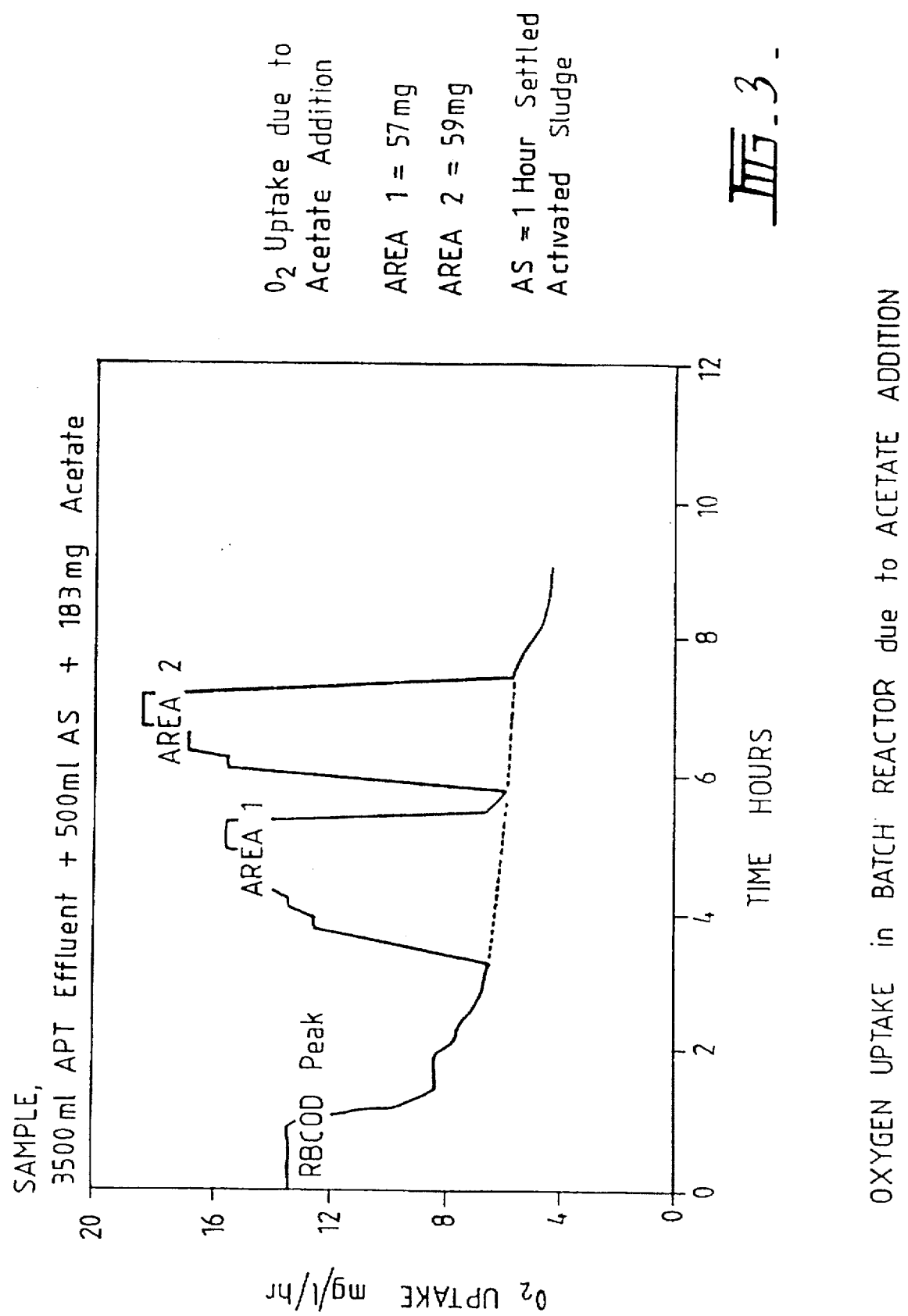
Figure 4:
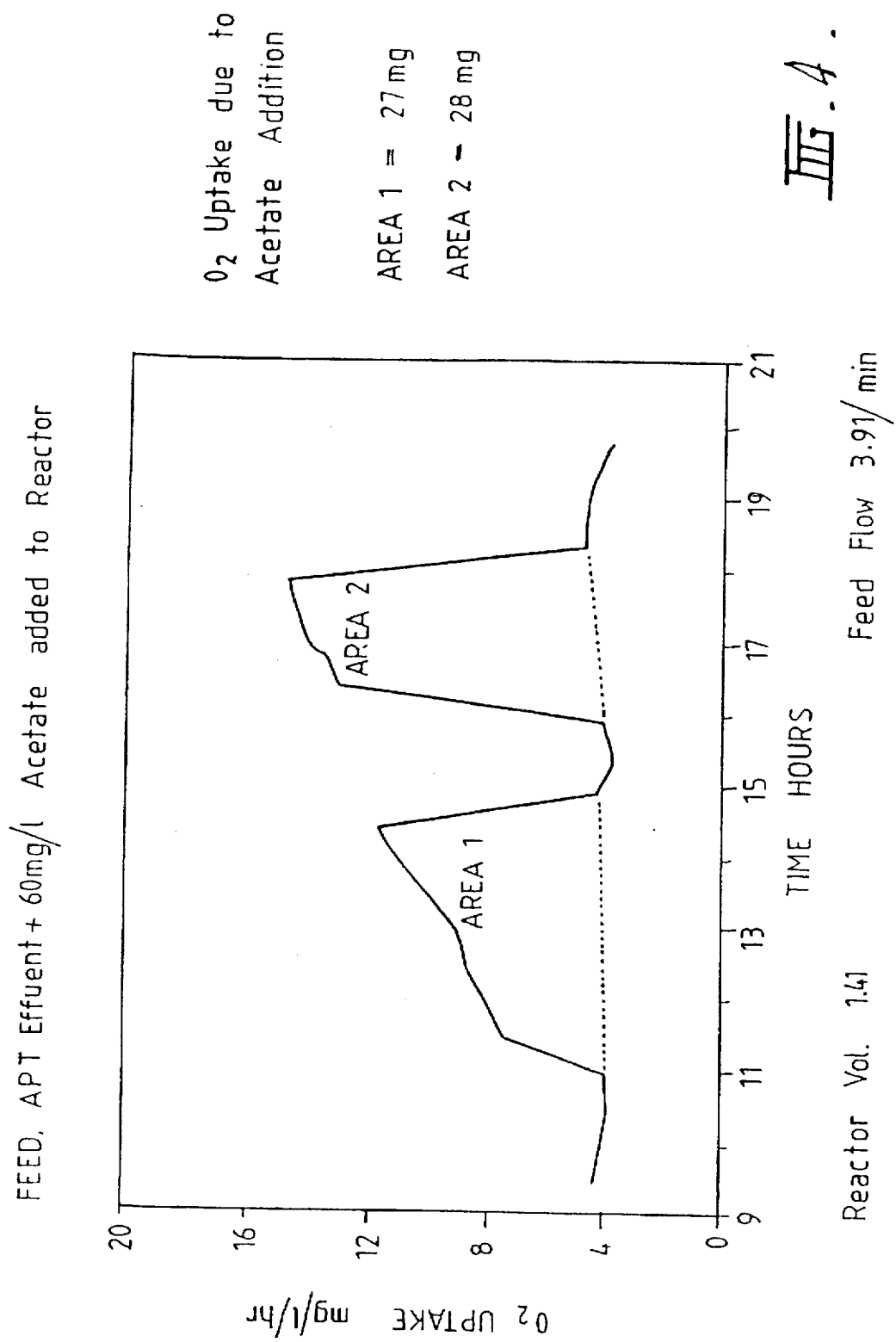
FIGS. 4 and 5 illustrate $O_2$ consumption in a reactor according to the invention due to Acetate addition.
Figure 5:
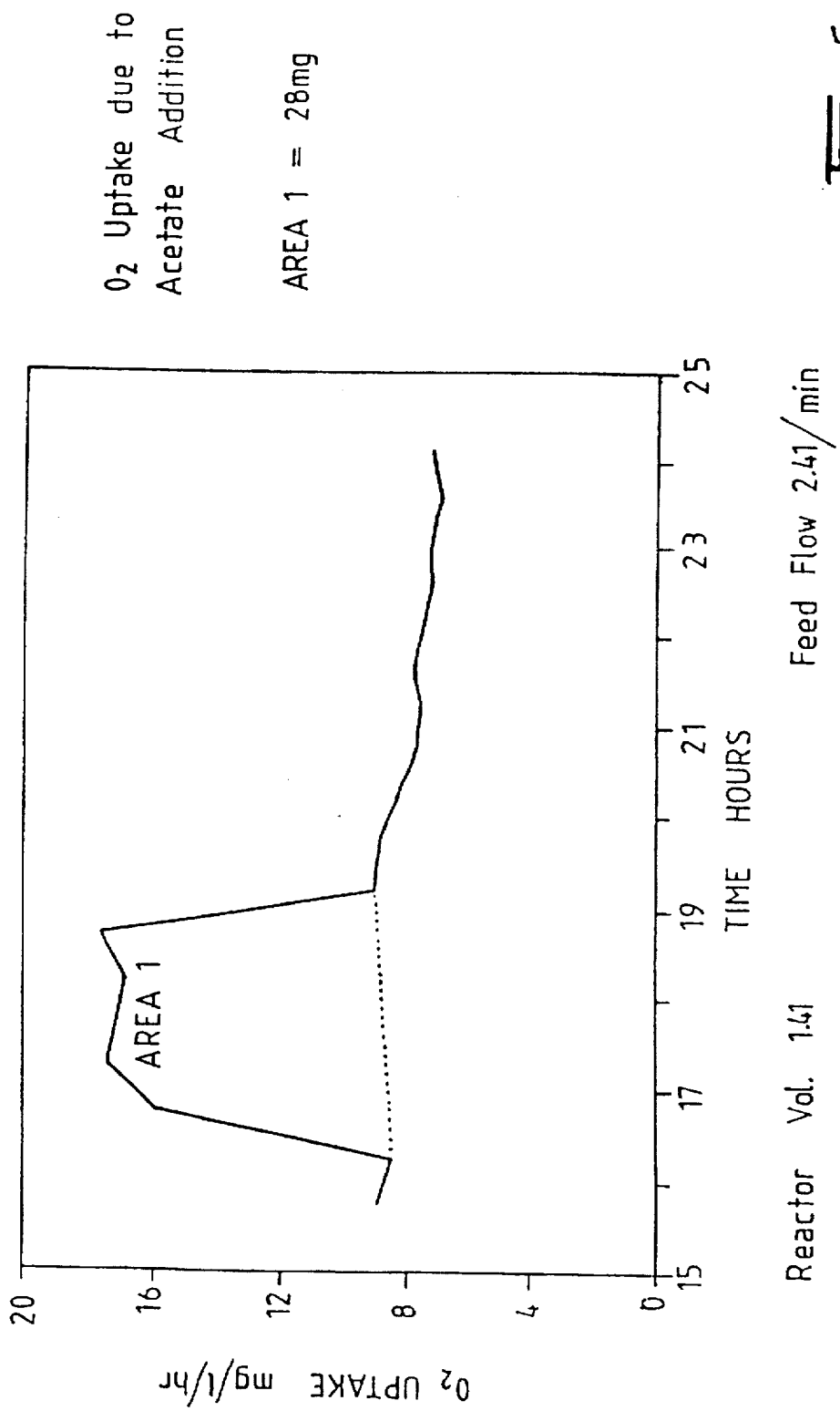

| | % of Chemical Oxygen Demand of Acetate | | | |
|---|---|---|---|---|
| | Batch | | Continuous | |
| | Area 1 | Area 2 | Area 1 | Area 2 |
| FIG. 2 | 29% | 29% | FIG. 4 | 29% | 31% |
| FIG. 3 | 29% | 31% | FIG. 5 | 30% | |

The above figures are in excellent agreement with each other, and when converted to RBCOD using the factor of 3 recommended by Dold et. al. (supra) give a result similar to that reported by Lindrea et. al. (1988) "The Determination of the Readily Biodegradable COD Fraction of Wastewater", Australian Water and Wastewater Association, 13th Federal Convention, Canberra, March 6–10, pp. 294–298.

The possibility existed that oxygen adsorption from the atmosphere may be occurring through the open top continuous reactors during the air off period. This would result in lower oxygen uptake readings, although the acetate addition results did not suggest this. Tight fitting closed cell foam disks were pressed into the reactors down to liquid surface level. No measurable difference was found in the oxygen consumption rate and as the discs only increase the surface area to volume ratio for biofilm growth, they may be dispensed with.

It was felt that these results were sufficiently encouraging for the apparatus to be used for the measurement of RBCOD in the influent and effluent streams of an activated primary tank (APT) of a 5.3 m$^3$ /day pilot sewage treatment plant operated by CSIRO at its Lower Plenty Research Station (Bayly et al "The Effect of Primary Fermentation on Biological Nutrient Removal" Australian Water and Wastewater Association, 13th Federal Convention, Canberra, Mar. 6–10, 1989, pp. 162–166). Excess phosphorous removal was associated with the pretreatment of the pilot plant feed by the APT, the purpose of which is to increase the concentration of influent RBCOD.

Continuous In Situ Measurement of RBCOD

One reactor was fed with raw screened sewage continuously pumped from the feed stream to the APT, the other with APT effluent which is used to feed the Bio-P removal pilot plant.

Figure 6:
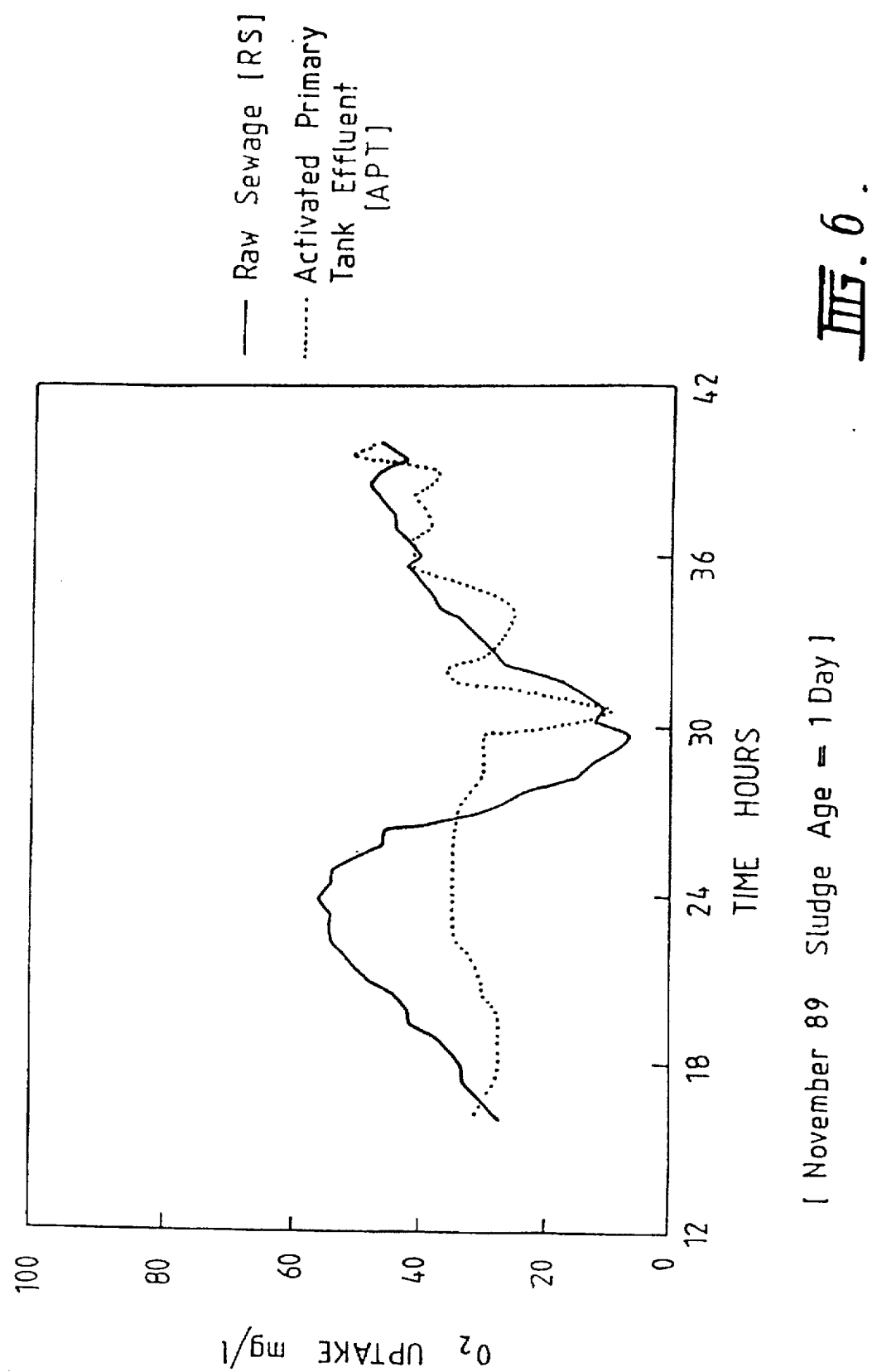
FIGS. 6 and 7 illustrate on-line operation of the method and apparatus of the invention.
Figure 7:
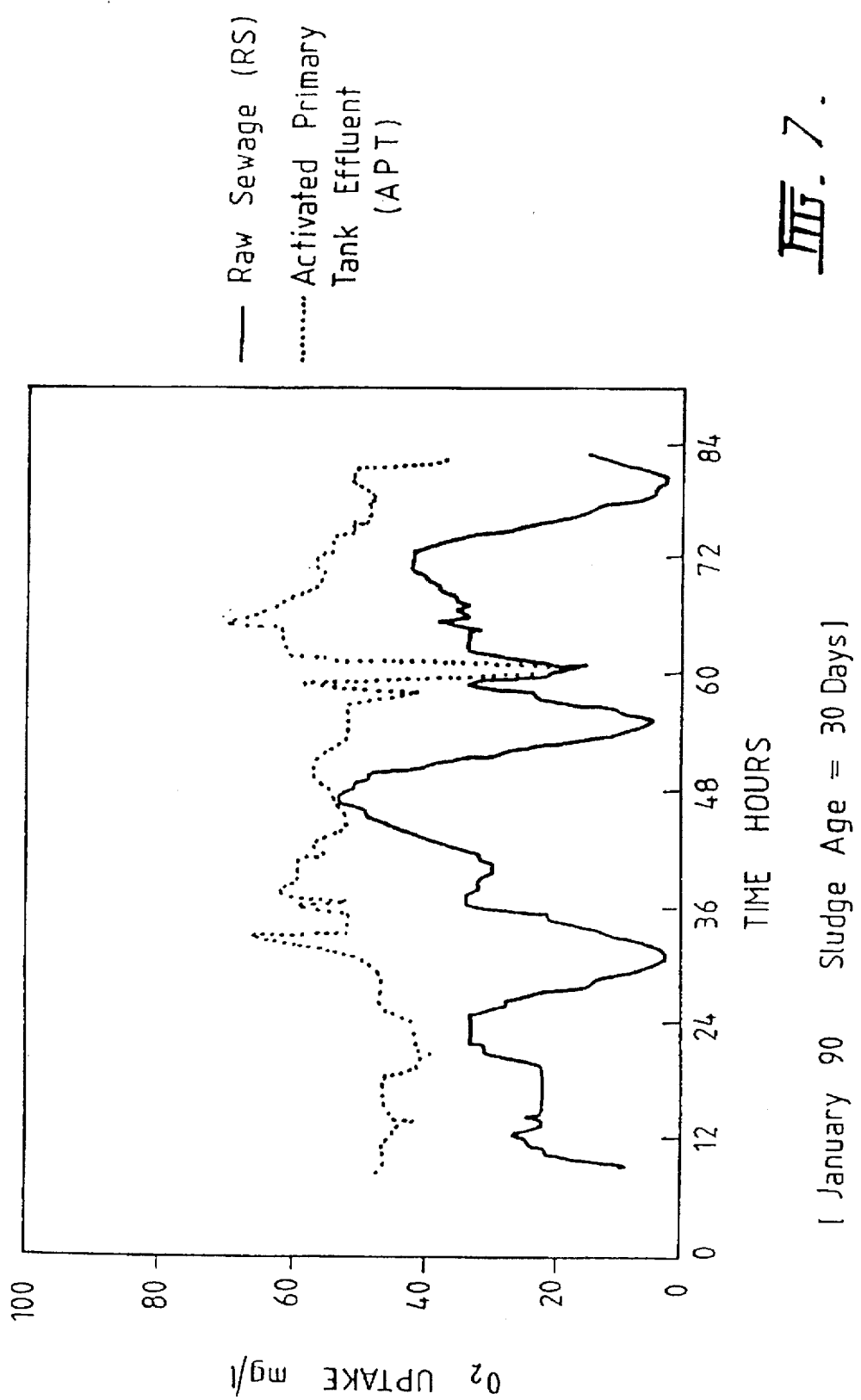

The data shown in FIG. 6 is typical of that collected during November 1989 when the APT was operating as a clarifier, the settled solids being drawn off once a day to give a sludge age of approximately one day. Under these conditions it appears that very little if any RBCOD was being generated, the average oxygen consumption values are, 37 mgO$_2$/l of influent and 33 mgO$_2$/l of effluent. In contrast FIG. 7 is typical of data collected during January 1990 when settled solids were being built up in the APT to obtain a sludge age of approaching 30 days. The average influent oxygen consumption for FIG. 7 is 26 mgO$_2$/l and effluent 51 mgO$_2$/l.

The diurnal pattern of raw sewage oxygen consumption can be clearly seen in FIG. 7. Typically a very low value occurs at about 6 to 7 am followed by an initial peak at about mid-day, a plateau or trough, then a second usually higher peak around 10 pm. The minimum diurnal value is in the region of 4 to 5 mgO$_2$/l and the maximum value between 40 and 60 mgO$_2$/l.

The effluent pattern is damped and moved in time by the APT hydraulic retention time HRT, which is variable with the diurnal feed rate. Also the feed rate to the APT dictates the degree of dilution of soluble substrates being produced from the accumulated settled solids. The dip in the curves at around 8 am is caused by flow cessation for routine reactor cleaning.

The continuous fed reactor returns similar oxygen uptake results to the batch method when calibrated by acetate addition. The method of the invention provides a convenient investigative adjunct to the well established batch method and provides a clearer picture of diurnal and day to day RBCOD variations. This information could be used to predict the performance of an operating process with or without an APT or be used for design of new plants.

Those skilled in the art will appreciate that the invention described herein is susceptible to variations and modifications other than those specifically described. It is therefore to be understood that the invention includes all such variations and modifications which fall within its spirit and scope.

I claim:

1. A method for periodically determining in real time the readily biodegradable chemical oxygen demands (RBCOD) in a wastewater stream or feed without adding sludge or biomass comprising:

i) feeding a portion of a wastewater stream or feed into a bioreactor without supplementary addition of sludge or biomass whereby a feed rate is controlled to ensure a hydraulic retention time (HRT) in the bioreactor sufficient for substantially complete oxidation of readily biodegradable compounds in the portion, ii) periodically passing air through the portion in the bio-reactor, iii) during periods when air is not passed through the portion in the bio-reactor, measuring oxygen consumption values of the portion in the bioreactor by measuring a change in the dissolved oxygen content over a measured time interval, and iv) calculating an RBCOD value for each of the measured oxygen consumption values by multiplying each measured oxygen consumption value by an apparatus constant.

2. The method of claim 1 wherein the bio-reactor is maintained at a substantially constant temperature.

3. The method of claim 1 wherein the portion in the bio-reactor is continuously stirred.

4. The method of claim 1 wherein a period for periodically passing the air through the portion in the bio-reactor together with one of the periods when the air is not passed through the portion in the bio-reactor is within the range of 1 to 30 minutes.

5. The method of claim 4 wherein the period for periodically passing the air through the portion in the bio-reactor together with one of the periods when the air is not passed through the portion in the bio-reactor is between 10 to 15 minutes.

6. A self-contained portable unit for measuring the readily biodegradable chemical oxygen demand (RBCOD) in a real time waste water system or feed without adding sludge or biomass, said self-contained portable unit comprising:

bio-reactor means not containing sludge or biomass for receiving a portion of a real-time waste water stream or feed;

means for providing the portion to the bio-reactor means at a controlled rate to ensure a hydraulic retention time (HRT) in the bio-reactor means sufficient for complete oxidation of readily biodegradable compounds in the portion;

air injection means, for periodically passing air through the portion in said bio-reactor means;

measuring means for measuring a change in the dissolved oxygen content over a measured time interval of the portion in said bio-reactor means to determine oxygen consumption values of the portion in said bio-reactor means during periods when air is not passed through the portion in the bio-reactor means;

data processing means in said bio-reactor means for calculating the readily bio-degradable chemical oxygen demand (RBCOD) for each of the measured oxygen consumption values by multiplying each measured oxygen consumption value by an apparatus constant and for producing electrical output signals representative of the calculated RBCOD; and a housing containing said bio-reactor means, said air injection means, said measuring means, and said data processing means.

7. The self-contained portable unit of claim 6, further comprising a pump, for supplying the portion to said bio-reactor means, said housing further containing said pump.

8. The self-contained portable unit of claim 6, further comprising means for maintaining the portion in said bio-reactor means at a substantially constant temperature.

9. The self-contained portable unit of claim 6, further comprising means for stirring the portion in said bio-reactor means.

10. The self-contained portable unit of claim 6, wherein said bio-reactor means includes an inlet and an overflow outlet, wherein the inlet receives the real-time waste water stream or feed.

11. The self-contained portable unit of claim 6, wherein said bio-reactor means includes means for cleaning an internal surface of said bio-reactor means.

* * * * *